(12) United States Patent
Maeda et al.

(10) Patent No.: US 8,558,193 B2
(45) Date of Patent: Oct. 15, 2013

(54) CHARGED PARTICLE BEAM DEVICE

(75) Inventors: Shusaku Maeda, Mito (JP); Kouji Ishiguro, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/382,396

(22) PCT Filed: May 14, 2010

(86) PCT No.: PCT/JP2010/003257
§ 371 (c)(1),
(2), (4) Date: Jan. 5, 2012

(87) PCT Pub. No.: WO2011/004533
PCT Pub. Date: Jan. 13, 2011

(65) Prior Publication Data
US 2012/0112068 A1   May 10, 2012

(30) Foreign Application Priority Data
Jul. 8, 2009  (JP) .................................. 2009-161383

(51) Int. Cl.
*G01N 23/225* (2006.01)
(52) U.S. Cl.
USPC ........ 250/443.1; 250/306; 250/307; 250/310; 250/311; 250/440.11
(58) Field of Classification Search
USPC ............ 250/306, 307, 309, 310, 311, 440.11, 250/443.1
See application file for complete search history.

(56) References Cited

U.S. PATENT DOCUMENTS

| 5,667,622 A | 9/1997 | Hasegawa et al. |
| 2004/0262515 A1 | 12/2004 | Motoi et al. |
| 2005/0230637 A1* | 10/2005 | Fukushima et al. ....... 250/443.1 |
| 2006/0054813 A1* | 3/2006 | Nokuo et al. ................. 250/307 |
| 2006/0063120 A1* | 3/2006 | Barlian et al. ................. 432/36 |
| 2008/0200100 A1* | 8/2008 | Takahashi et al. .............. 451/44 |
| 2009/0017733 A1* | 1/2009 | Takahashi et al. .............. 451/57 |
| 2011/0098960 A1 | 4/2011 | Mizuochi |

FOREIGN PATENT DOCUMENTS

| JP | 06-260126 A | | 9/1994 |
| JP | 08255819 A | * | 10/1996 |
| JP | 9-205080 A | | 8/1997 |
| JP | 11-168056 A | | 6/1999 |
| JP | 2003-133402 A | | 5/2003 |
| JP | 2003133402 A | * | 5/2003 |
| JP | 2003-194746 A | | 7/2003 |
| JP | 2005-340719 A | | 12/2005 |
| JP | 2006-105960 A | | 4/2006 |
| JP | 2008-010259 A | | 1/2008 |
| JP | 2009-064726 A | | 3/2009 |
| JP | 2010-15732 A | | 1/2010 |

* cited by examiner

*Primary Examiner* — Michael Logie
(74) *Attorney, Agent, or Firm* — Miles & Stockbridge P.C.

(57) ABSTRACT

The present invention provides a charged particle beam device in which the change of expansion/contraction of a specimen which is an observing object is restricted thereby eliminating position deviation of the observing object and significantly increasing its throughput. The present invention includes specimen holding means for holding a specimen, temperature regulation means which can regulate the temperature of the specimen, and temperature regulation means control means which can control the temperature regulation means based on various conditions.

12 Claims, 8 Drawing Sheets

Fig. 4
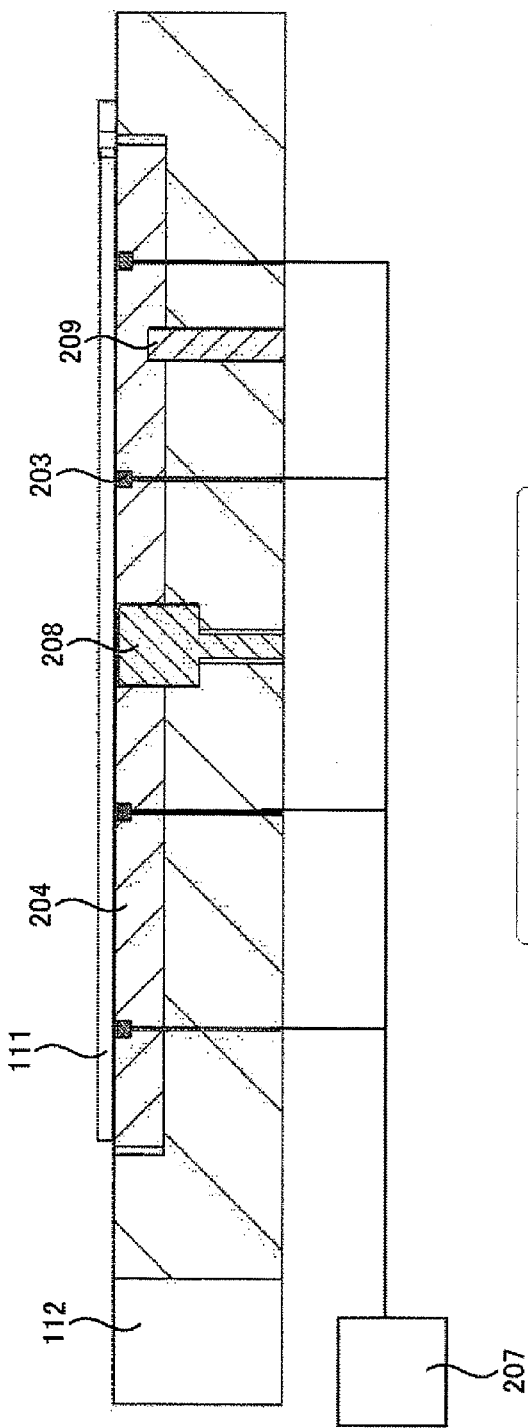
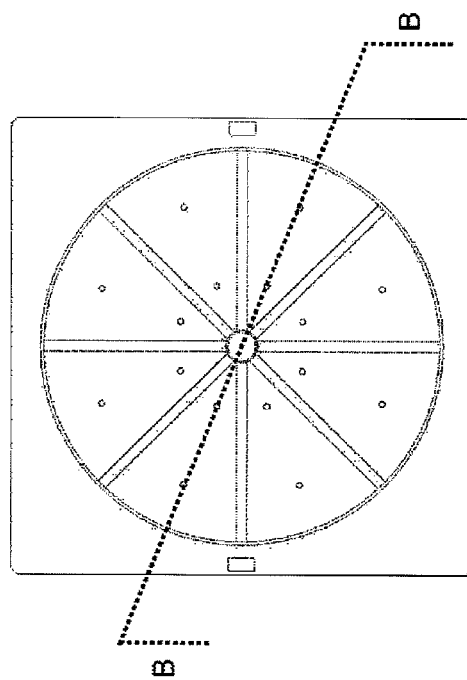

CHARGED PARTICLE BEAM DEVICE

TECHNICAL FIELD

The present invention relates to charged particle beam devices such as electron microscopes and ion beam processing/observation apparatuses and the like, and temperature regulation means of a specimen to be observed by a charged particle beam device.

BACKGROUND ART

In the fields of manufacturing, inspection, and evaluation of semiconductor devices in which miniaturization is advancing at an accelerated pace, in order to produce devices more efficiently, the inspection and measurement of semiconductor wafers during a manufacturing process has been becoming increasingly important. As the inspection and measurement apparatus of semiconductor wafers during the manufacturing process, various apparatuses employing a charged particle beam are in use. For example, a CD-SEM is used for the measurement of the pattern width of a resist pattern, an electron beam external appearance inspection apparatus is used for defect position detection after wiring formation, and a review SEM is used for defect classification; all these apparatuses are based on scanning electron microscopy technology. Moreover, it is sometimes necessary to observe the defect region that has been detected, by a transmission electron microscope at a high magnification; in such cases, an ion beam processing system is used when cutting out the defect region from the wafer to produce a sample for the transmission electron microscope.

While a wafer is processed with various apparatuses such as for manufacturing, inspection, evaluation and so on to be made into a product as a device, a wafer is placed on a specimen stage, and the specimen stage is moved by a stage transport apparatus in various kinds of wafer processing apparatuses. In the above described charged particle beam inspection and measurement apparatus, it is necessary that the specimen stage with a wafer which is transported from another apparatus placed thereon transports the observation spot of the wafer to a predetermined location it its own apparatus, such as the electron beam irradiation position of the electron microscope. As described so far, while the wafer is processed through several kinds of manufacturing, inspection, and evaluation apparatuses, since a position repeatability in nano-order is required between the respective apparatuses, an origin point adjustment and alignment at a specific point are performed for each apparatus where the processing is performed to create a coordinate system in the current apparatus so that timing to start transporting the wafer, stopping position thereof, and the like are controlled based on the coordinate system.

There are two major factors that affect the transport accuracy of the wafer; one is the mechanical accuracy of the transport apparatus itself, and the other is the expansion of the wafer due to heat. Regarding the former factor, although it has become possible to obtain a braking performance in sub-micron order owing to improvements of the transport apparatus, since it is still difficult to obtain a braking performance in nano order because of the limitation of mechanic control, the above described position repeatability is ensured by acquiring a low magnification image for the confirmation of irradiation position of charged particle beam before acquiring a high magnification image necessary for wafer processing, and to judge the detailed position of the measuring object. It is noted that, in such a case, if the position deviation is so large that the observing object moves out of the field of view of low magnification, the wafer alignment needs to be performed again and thereby the throughput of wafer processing is significantly reduced.

The latter factor of the expansion of the wafer due to heat is a problem that has long been known in the field of semiconductor manufacturing equipment such as ion implantation apparatus, exposure apparatus, and the like. For example, JP Patent Publication (Kokai) No. 9-205080A (1997) (Patent Literature 1) discloses an invention in which a Peltier element is built into a wafer-opposing surface of an electrostatic chuck for holding the wafer, and a thermocouple is disposed above the Peltier element (in the wafer-opposing surface) so that the Peltier element is controlled by the temperature of the wafer sensed by the thermocouple. Further, JP Patent Publication (Kokai) No. 2008-010259A (2008) (Patent Literature 2) discloses a patent of an exposure apparatus in which heating means and a temperature sensor are disposed in an electrostatic chuck, and the above described heating means is heated so as to correct partial distortion of the wafer due to electron beam heating.

The reason why the temperature control technique for the wafer as described above has developed in semiconductor manufacturing equipment is that the requirement for the accuracy of beam irradiation position control is rigorous since redoing is not allowed in the case of manufacturing in contrast to the cases of inspection and measurement. Moreover, in inspection and measurement apparatuses, in order to acquire a high resolution image, in the case of a wafer inspection and measurement apparatus utilizing a charged particle beam, since it is necessary to scan a primary charged particle beam which is focused as narrowly as possible on the specimen, and therefore the beam current cannot be increased very high in terms of the Coulomb effect, the energy of the charged particle beam to be launched into the wafer is small in the wafer inspection and measurement apparatus utilizing a charged particle beam compared with the semiconductor manufacturing equipment, and therefore a position deviation caused by the expansion of the wafer due to heating by charged particle beam has not become a serious problem.

CITATION LIST

Patent Literature

Patent Literature 1
JP Patent Publication (Kokai) No. 9-205080A (1997) (U.S. Pat. No. 5,567,622)
Patent Literature 2
JP Patent Publication (Kokai) No. 2008-010259A (2008)

SUMMARY OF INVENTION

Technical Problem

As described above, in the case of a charged particle beam inspection and measurement apparatus which picks up an image by scanning a primary charged particle on a specimen, and acquiring generated secondary charged particle beam, an expansion of the wafer due to heating by charged particle beam irradiation has not become a serious problem in the past. However, in recent years, a problem has surfaced that the wafer expands due to the heat generated in the wafer transport apparatus. Hereafter, details thereof will be described.

For a wafer inspection and measurement apparatus utilizing a charged particle beam, there is always a demand to increase the speed of wafer processing, that is, to reduce the time needed to perform predetermined processing per one sheet of semiconductor wafer. One of the largest factors that determine the throughput of wafer processing of various apparatuses includes a wafer transport speed. In recent wafer inspection and measurement apparatuses, as the demand for increasing the speed of wafer processing or increasing the number of measurement and inspection points grows, there arises the need for moving the specimen stage substantially faster than before. Since the specimen stage is stopped during image pick-up, moving the specimen stage at a high speed means that rapid controlled motion such as rapid acceleration and sudden stopping are repeated many times. While a stage transport apparatus includes driving means such as a linear motor, an ultrasonic motor, or a combination of a ball screw and a pulse motor; in any case, heat generation at the sliding portion is unavoidable. Moreover, as the moving speed of the specimen stage increases, the amount of heat generation will increase. Therefore, even when the stage is continuously moved at a constant speed, if the moving speed is increased, the amount of heat generated at the transport apparatus increases, and thereby the expansion of the wafer becomes a problem.

On the other hand, when performing temperature control of the wafer in a wafer inspection and measurement apparatus using a charged particle beam, there is a task to restrict the occurrence of foreign materials. While, in the invention disclosed by Patent Literature 1, a thermocouple is brought into contact with the back side of the wafer to detect the temperature of the wafer, such contact will cause the occurrence of foreign materials. Since the foreign material that has occurred flies up during the transport of the wafer, it may cause sticking of foreign material on the wafer surface and pollution thereof. Moreover, in some manufacturing processes such as light exposure, foreign materials on the back side of the wafer may cause a problem. This is because the change of the height of the wafer due to the presence or absence of the foreign material on the back side may cause a focus deviation. In the case of a wafer inspection and measurement apparatus, since it will not be allowed that the quality of processing object changes between before and after inspection and measurement, when the temperature control of the wafer is performed in a wafer inspection and measurement apparatus utilizing a charged particle beam, it is required to perform the temperature measurement of the wafer to restrict the occurrence of foreign materials or the measurement of variation amount in wafer size.

Solution to Problem

In order to achieve the above described objects, the present invention provides a temperature regulation unit in a specimen holding unit for holding a semiconductor wafer which is the specimen, and a measurement unit for acquiring an observation indication of the wafer, which is necessary for controlling the temperature regulation unit in a contactless manner.

Advantageous Effects of Invention

According to the present invention, even if heat is generated due to any kind of causes such as heat generation at mechanical portions due to continuous driving of specimen stage or the like, the temperature of a wafer 111 and the wafer holding mechanism will not change. This will result in that there is no need of redoing the alignment, and performing comparison operation between an observing object image and a reference image at a low magnification, and it becomes possible to observe the measuring object without causing position deviation thereof, thus significantly improving the throughput.

BRIEF DESCRIPTION OF DRAWINGS

FIG. 4 is a cross sectional view No. 2 of the specimen holding portion in the charged particle beam device of Embodiment 1.

DESCRIPTION OF EMBODIMENTS

Hereafter, embodiments will be described with reference to the drawings.

Embodiment 1

In the present embodiment, description will be made on a configuration example of a charged particle beam device including an infrared sensor as measurement means for acquiring in a contactless manner an observation indication of a wafer which is needed for controlling temperature regulation means. Further, the present embodiment will be described by taking a scanning electron microscope as an example of the charged particle beam device, the scanning electron microscope having a function of detecting secondary electrons or reflected electrons which are generated by irradiating a wafer with a primary electron beam.

Figure 1:
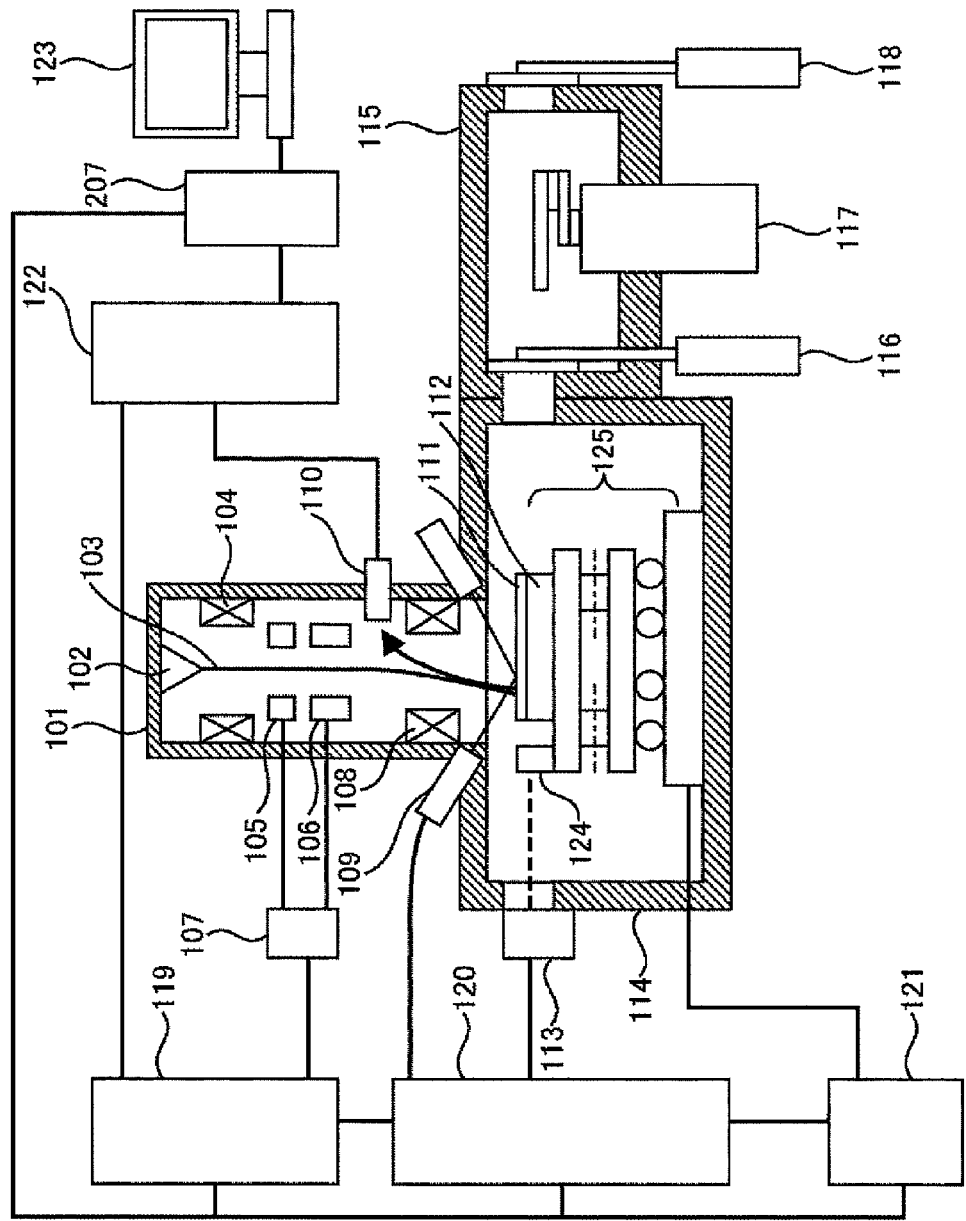
FIG. 1 is a plan view to show a general configuration of a scanning electron microscope which is an embodiment of the present invention.

FIG. 1 shows a general view of a scanning electron microscope of the present embodiment. Broadly divided, a typical scanning electron microscope is made up of a column 101, a specimen chamber 114, and a load lock chamber 115. Hereafter, a series of sequence for observing a wafer 111 which is the observing object will be described. First, the wafer 111 is transported from a wafer transport apparatus (not shown) outside the equipment, so that after an atmospheric-side gate valve 118 is opened, the wafer 111 is carried into the load lock chamber 115, and after the atmospheric-side gate valve is closed, the load lock chamber 115 is evacuated by a vacuum pump (not shown). Thereafter, a vacuum-side gate valve 116 is opened and the wafer 111 is carried into the specimen chamber 114 by a vacuum transport robot 117. In the present embodiment, although it is assumed that the wafer transport from the load lock chamber 115 to the specimen chamber 114 is performed by the vacuum transport robot 117, the wafer 111 may be carried into the specimen chamber 114 by using a wafer holder and the like. In this case, a wafer holding mechanism 112 may be equipped in the wafer holder, or the wafer holder itself may have a function equivalent to that of the wafer holding mechanism 112. It is noted that the interior of the specimen chamber 114 is always kept evacuated.

The wafer 111 which has been carried into the specimen chamber 114 is placed onto the wafer holding mechanism 112 on a specimen stage 125. The specimen stage 125 is driven via a stage control unit 121 by using transport means in which a ball screw and a pulse motor are combined, or other transport means such as a linear motor and an ultrasonic motor or the like. A bar mirror 124 is attached onto the specimen stage 125, so that the position of the wafer 111 mounted and held on the specimen stage 125 is monitored by measuring the position of the specimen stage 125 by performing a laser measurement of the change of relative distance between an interferometer 113 attached to the specimen chamber 114 and the bar mirror 124, and performing processing thereof at a position control unit 120. Here, to detect the position of the specimen stage 125, position detection means such as a linear scale and the like may be used.

A charged particle beam 103 is generated from an electron gun 102 in the column 101, and this charged particle beam 103 passes through an electron lens 104 and an object lens 108. Moreover, deflection coils 105 and 106 are provided in the column 101, and the charged particle beam 103 generated from the electron gun 102 is deflected into a predetermined trajectory by a deflection control unit 107. The charged particle beam 103 is converged by the above described object lens 108 and is irradiated to the wafer 111. When the charged particle beam 103 is irradiated onto the wafer 111, reflected electrons and secondary electrons are generated, and are detected by a detector 110. The detection signals of the reflected electrons and secondary electrons detected by the detector 110 are inputted to an image control unit 122 along with control information of the charged particle beam 103 by the deflection coils 105 and 106. In the image control unit 122, image data is created based on the above described information and is displayed on a monitor 123. It is noted that a height detection sensor 109 is equipped in the scanning electron microscope in the present embodiment, which detects a precise height of the wafer 111 which is the observing object, and based on that, the deflection amount, convergence rate, and the like of the charged particle beam 103 are determined at a column control unit 119. A temperature regulation mechanism control unit 207 for controlling temperature regulation means provided on the specimen stage 125 is disposed between a monitor 123 and the image control unit 122. The operation and function of the temperature regulation mechanism control unit 207 will be described later.

Figure 2:
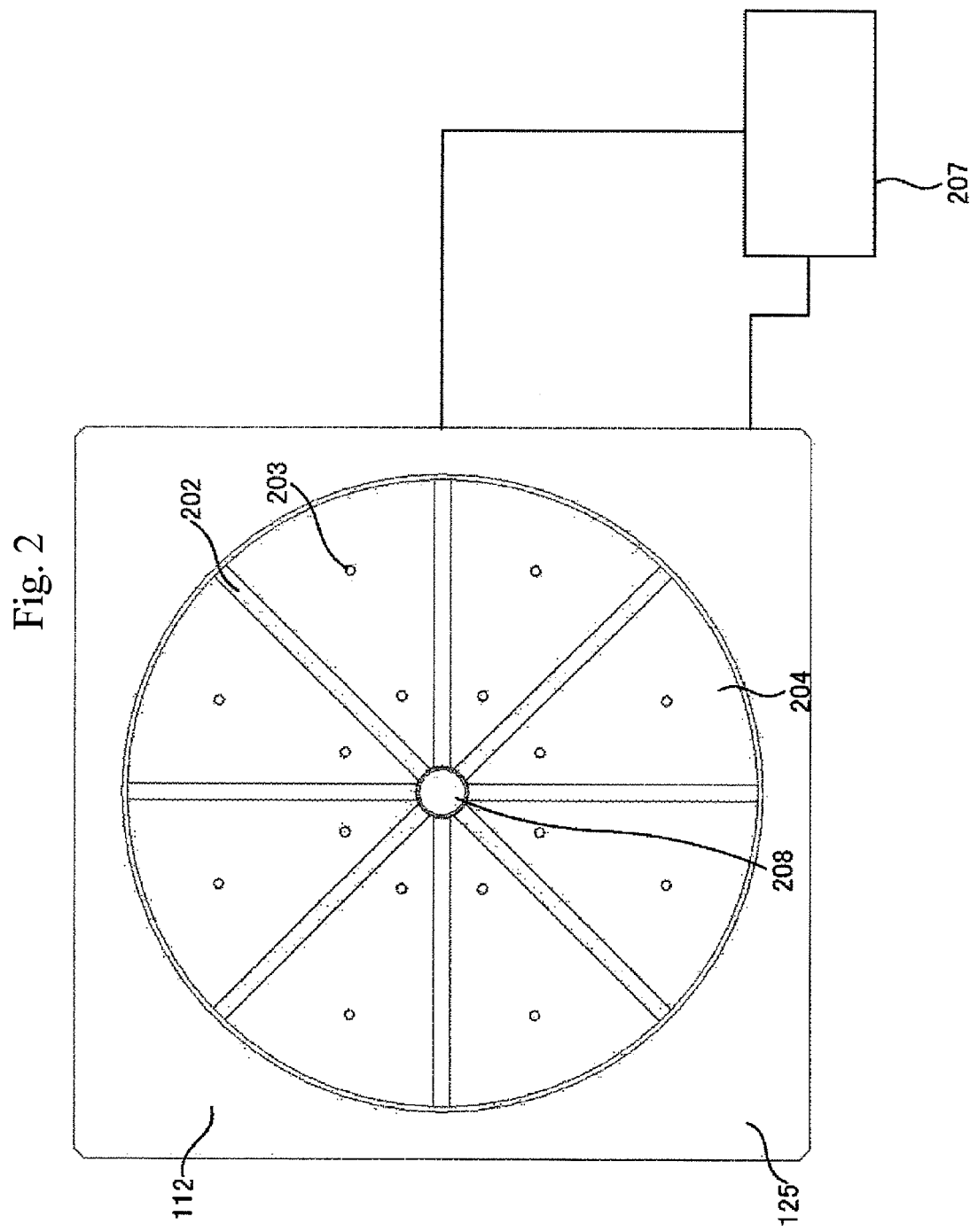
FIG. 2 is a top view of a specimen holding portion in a charged particle beam device of Embodiment 1.
Figure 3:
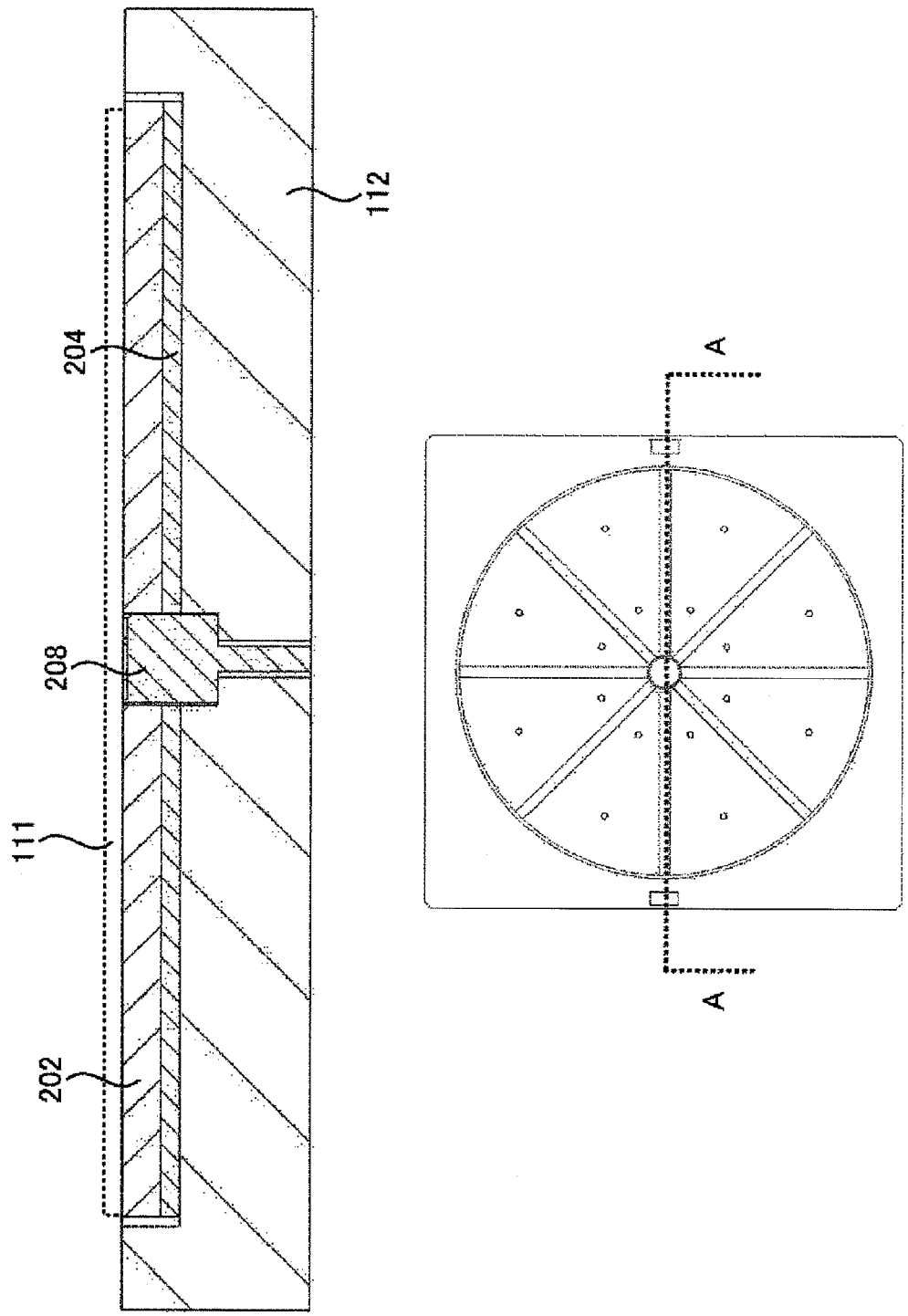
FIG. 3 is a cross sectional view of the specimen holding portion in the charged particle beam device of Embodiment 1.

Next, using FIGS. 2, 3, and 4, the details of the specimen stage of the present embodiment will be described. FIG. 2 shows a top view of the wafer holding mechanism 112 of the present embodiment. As described above, the wafer 111 is transported from the wafer transport apparatus (not shown) to be carried into the load lock chamber 115, which thereafter is evacuated. After completion of evacuation, the wafer 111 is transported to the wafer holding mechanism 112 in the specimen chamber 114 and is adsorbed and fixed to an electrostatic adsorption plate 204 of the electrostatic chuck. Although an electrostatic chuck is used as the fixing means of the wafer 111 in the present embodiment, a mechanical chuck and the like may be used. There are provided in the center of the electrostatic adsorption plate 204 a pusher pin 208 for stripping off the wafer after wafer processing, and an opening through which the pusher pin is moved up and down, and a temperature regulation mechanism 202 and a temperature measurement sensor 203 are disposed around the opening.

In the present embodiment, a Peltier element having a tabular upper electrode is used as the temperature regulation mechanism, and such tabular Peltier elements are disposed centering around the pusher pin and radially toward the outer periphery of the electrostatic chuck. Moreover, a total of 16 of the temperature measurement sensors 203 are disposed in a concentric fashion around the pusher pin 208 with eight of them being in the inner peripheral portion around the central portion of the electrostatic adsorption plate and eight of them being in the outer peripheral portion near the edge of the electrostatic adsorption plate. Since the wafer 111 on the electrostatic adsorption plate 204 has no fulcrum, it is more likely to change radially when expanding or contracting due to temperature change. Therefore, disposing the Peltier elements radially from the center allows uniform heat transfer to and from the wafer, thereby enabling to perform smooth temperature regulation and to prevent an excessive stress from being applied to the wafer due to its expansion/contraction. Furthermore, radially disposing the temperature measurement sensors in a similar manner enables to uniformly measure the wafer temperature and to feedback accurate temperature information to the above described Peltier elements. Combining such arrangements will enable to regulate the temperature of the wafer 111 efficiently in real time.

The temperature measurement sensor 203 is attached to the inside of the wafer holding mechanism 112 and measures the temperature of the wafer in a contactless manner. The measured temperature is accumulated through an internal cable of the wafer holding mechanism 112 into the temperature regulation mechanism control unit 207, and a voltage to be applied to the Peltier element is calculated at the temperature regulation mechanism control unit 207 so that the voltage is applied to the temperature regulation mechanism 202 through an electrostatic adsorption plate power supply unit 209. Thereafter, according to an interval which is set before the processing of the wafer 111, temperature measurement is performed and the results thereof are accumulated as needed. Therefore, the temperature regulation mechanism control unit 207 includes a memory element for storing temperature information and a calculation element for calculating a voltage to be applied to the Peltier element from the temperature information.

The temperature measurement sensor of the present embodiment is required to measure the temperature of the wafer in a contactless manner. Therefore, an infrared sensor is used as the temperature measurement sensor. In order to describe this, a cross sectional view of a specimen holding means of the present embodiment is shown in FIGS. 3 and 4. FIG. 3 is a cross sectional view of the top view of the specimen holding means shown in FIG. 2 taken along a section (A-A section) including a tabular temperature regulation mechanism, and FIG. 4 is a cross sectional view of the top view of the specimen holding means shown in FIG. 2 taken along a section (B-B section) including the infrared sensor. The electrostatic adsorption plate 204 is provided with a through hole for disposing the infrared sensor and a cable to be connected to the sensor, and the infrared sensor is disposed in the through hole keeping a certain distance so as not to contact the wafer 111. Moreover, the electrostatic adsorption plate 204 is provided with fine irregularities on its surface (not shown) to reduce the contact area with the wafer so that the occurrence of foreign materials is reduced.

The specimen stage 125 repeatedly moves the measuring target position in the surface of the wafer 111 to the irradiation position of the charged particle beam 103 depending on the conditions. As a result of the movement as described above being repeated, heat is generated from the driving portion and the guide portion of the specimen stage 125, other contact portions and the like, thereby causing the temperature of the components making up the equipment such as the specimen stage 125 and the wafer holding mechanism 112 to rise. Therefore, the specimen stage is heated during wafer observation, and thus the temperature of the wafer placed onto the specimen stage will rise. The heated wafer expands according to its linear expansion coefficient thereby changing the coordinate system acquired by wafer alignment so that even if the specimen stage is moved to an ideal position in its own coordinate system, an actual observing object will be deviated from the electron beam irradiation position.

According to the charged particle beam device of the present embodiment, the temperature regulation mechanism control unit 207 determines a preset temperature based on the temperature measurement result which is accumulated as needed, and sets the temperature regulation mechanism 202 at a specified temperature so that the temperature of the wafer 111 is always constant. According to the flow described above, the temperature measurement and temperature regulation of the wafer 111 are repeated as needed. As a result of this, it is prevented that the temperature variation of the wafer 111 increases to or above a predetermined value during inspection and measurement of one wafer, and it becomes possible to restrict a position deviation due to the expansion of the wafer.

It is noted that while an example of the temperature regulation mechanism 202 includes a Peltier element or the like in the present embodiment, any other temperature regulation mechanism may be used provided that it can be installed in vacuum and has high temperature-responsiveness. For example, a temperature regulation mechanism may be obtained by forming a flow path through which refrigerant flows in the electrostatic adsorption plate, and circulating an appropriate refrigerant such as helium gas or chlorofluorocarbon, or a liquid such as water, therethrough. Moreover, although the number of installation of the infrared sensors is assumed to be 16 as shown in FIG. 2 in the present embodiment, the number of installation may be reduced according to the limitation of cost and arrangement of the mechanism. For example, since Si which is a principal component of the wafer 111 has a large thermal conductivity of about 150 [W/m·K], installing the temperature sensors, for example, only in the vicinity of the center will not significantly impair the performance of the mechanism.

Embodiment 2

While, in Embodiment 1, a charged particle beam device which is configured to acquire an observation indication (temperature in this case) of the wafer by an infrared sensor in a contactless manner has been described; in the present embodiment, an configuration example of a charged particle beam device which measures the variation of the diameter of the wafer thereby controlling the temperature regulation mechanism will be described. While the present embodiment will also be described by taking an example of a scanning electron microscope as the charged particle beam device, since the general configuration of the device is substantially similar to that of FIG. 1, description thereof will be omitted.

Figure 5:
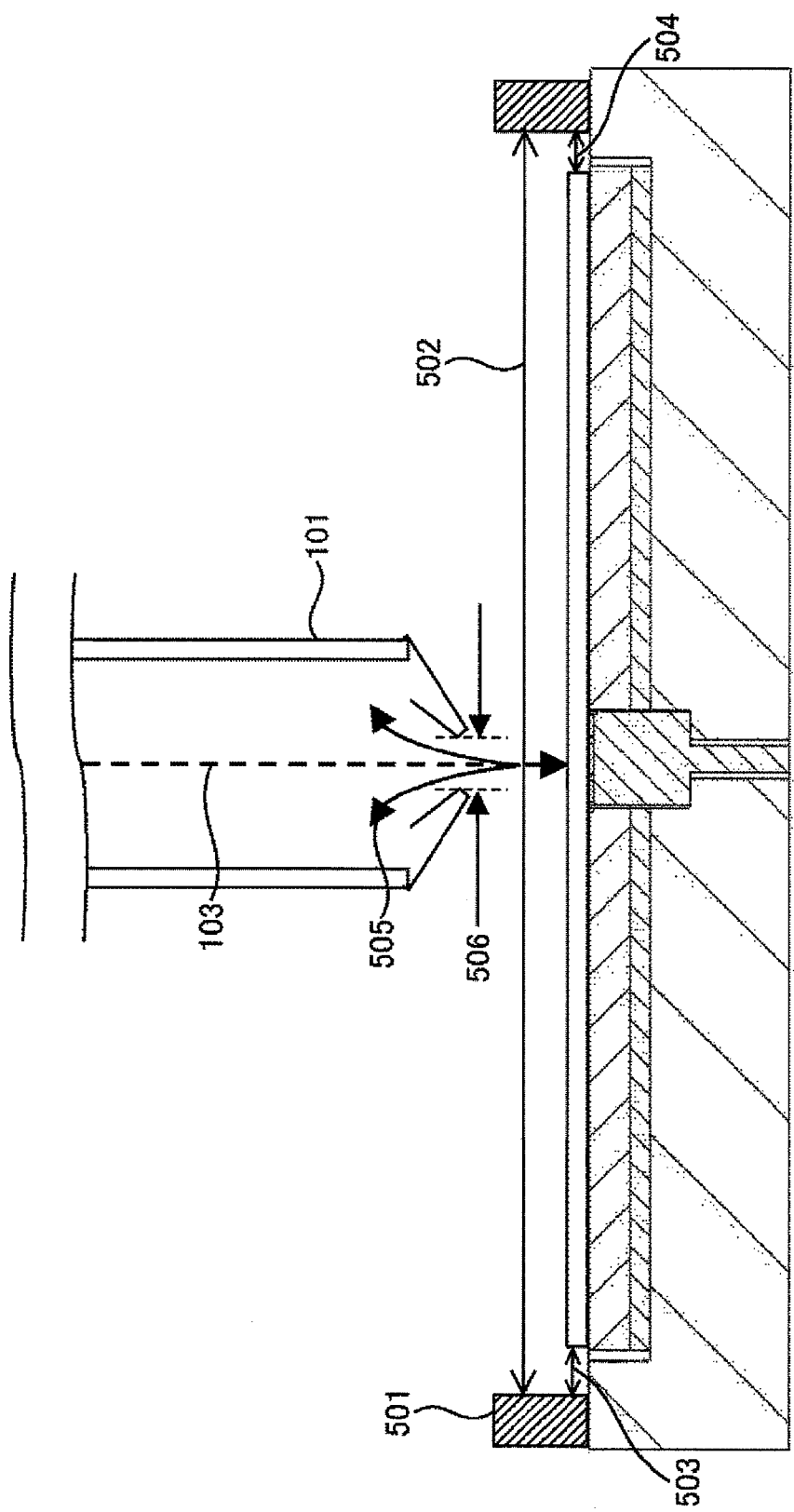
FIG. 5 is a cross sectional view of the specimen holding portion in the charged particle beam device of Embodiment 2.

FIG. 5 shows a cross sectional view of the wafer holding mechanism 112 of the present embodiment, along with the end portion of a charged particle beam column 101. Although the charged particle beam device of the present embodiment includes a Peltier element having a tabular upper electrode similar to that of Embodiment 1 as the temperature regulation mechanism, it does not include any temperature measurement sensor like an infrared sensor. Therefore, for the cross sectional view of the wafer holding mechanism, only a cross sectional view taken along a section including a tabular electrode of the Peltier element will be shown.

As in Embodiment 1, the wafer 111 is transported from a wafer transport apparatus (not shown) to be carried into the load lock chamber 115, which thereafter is evacuated. After completion of evacuation, the wafer 111 is transported onto the wafer holding mechanism 112. Thereafter, the diameter of the wafer 111 is measured by a pair of displacement sensors 504 installed on the wafer holding mechanism 112. Since the wafer 111 to be inspected or measured has a diameter of a value based on certain standards such as 150, 200, 300, and 450 mm etc., it is also possible to detect abnormalities such as a crack and a transport failure of the wafer 111 by comparing its diameter with a certain fixed value of normal range.

The displacement sensor 501 continuously performs the measurement of the wafer diameter basically during processing of the wafer 111. Moreover, the measurement of diameter is performed at intervals that are as short as possible to accumulate data in the temperature regulation mechanism control unit 207. The temperature regulation mechanism control unit 207 calculates the variation amount of the diameter of the wafer 111 from the accumulated result, and determines a preset temperature of the temperature regulation mechanism 202. This is used to control the temperature of the wafer 111. The displacement sensor of the present embodiment is based on an optical scheme, in which a laser beam emitted from one displacement sensor is sensed by the other displacement sensor 501, and from the time difference, the travel distance of the laser beam is measured at a high precision. To measure the diameter of the wafer, measurement is made by calculating the difference between the distance 502 between the two displacement sensors, and the distances 503 and 504 between the edge of the wafer and the two displacement sensors shown in FIG. 5. On this occasion, there are two ways of measurement, which are a method of measuring only the distances 503 and 504, and a method of always measuring the distance 502 in addition to the distances 503 and 504, and it is possible in principle to determine the diameter of the wafer by measuring only the distances 503 and 504 as the measurement value measured in real time. However, since the entire specimen stage is heated in reality due to the heat generated at the transport means, it is desirable to measure the distance 502 as well to perform high-precision measurement.

Here, the relationship between the measurement result of the diameter of the wafer 111 and the temperature rise can be simply determined from the linear expansion coefficient as shown by Equation (1) below.

[Formula 1]

$$\Delta T = \frac{\Delta L}{\alpha \times L} \qquad \text{(Formula 1)}$$

Where, reference symbols denote that ΔL: wafer expansion/contraction amount, ΔT: wafer temperature rise, L: wafer diameter, α: wafer (Si) linear expansion coefficient.

For example, if a diameter obtained by the displacement sensor 206 is 300.001 [mm] when the wafer 111 has a diameter of 300,000 [mm], and a linear expansion coefficient of 0.0000026 [1/° C.], the following relation holds: 300,001-300,000=0.0000026×300,000×ΔT and therefore:

ΔT=1.28° C.

thus, from the obtained temperature change amount, a preset temperature of the temperature regulation mechanism 202 is determined by the temperature regulation mechanism control unit 207. However, in the case of a complicated configuration, the temperature change may be determined by using a relation which is determined experimentally in advance.

Here, when the distance 502 is measured as well, a problem as shown below will arise. While the wafer is moved by the stage movement such that a predetermined position on the wafer corresponds to the irradiation position of electron beam, depending on the inspection and measurement position, there may be cases in which the primary electron beam optical axis radiated from the electron source crosses the optical path of laser radiated from the displacement sensor. FIG. 5 shows a state in which the primary electron beam 103 that falls down from the charged particle column 101 intersects with the optical axis of the laser beam radiated from the displacement sensor 501. In the case as shown in FIG. 5, in addition to the primary electron beam, the secondary electrons and reflected electrons 505 generated by electron beam irradiation will also intersect with the optical axis of the laser light. Since the laser is light, it will not directly interfere with the primary electron beam and the secondary electrons; however, it is problematic in terms of equipment design that the detection condition of the secondary electrons and reflected electrons 505 is different from that in other regions.

Accordingly, when the distance 502 is measured as well, in the present embodiment, the position control unit 120 transmits information of the irradiation position of the primary electron beam (the inspection or measurement region on the wafer) to the temperature regulation mechanism control unit 207 so that when inspection or measurement of a region where the primary electron beam optical axis may intersect with the optical path of laser is performed, the temperature regulation mechanism control unit 207 controls the laser irradiated from the displacement sensor 501 to be turned off. Moreover, there is provided in the bottom portion of the charged particle column an opening 506, through which the primary electron beam and the secondary electrons are made to pass through and which has a certain diameter as shown in FIG. 5. Since the secondary electrons and reflected electrons generated from the specimen reach the detector 110 as being expanded to be larger than the diameter of the primary electron beam, in order to equalize the detection condition of the secondary electrons and reflected electrons 505 to those of other regions, the laser beam is turned off at least when the region through which the laser beam passes through on the wafer corresponds to the region having an area as large as that of the opening 506, which centers around the landing point of the primary electron beam.

Figure 6:
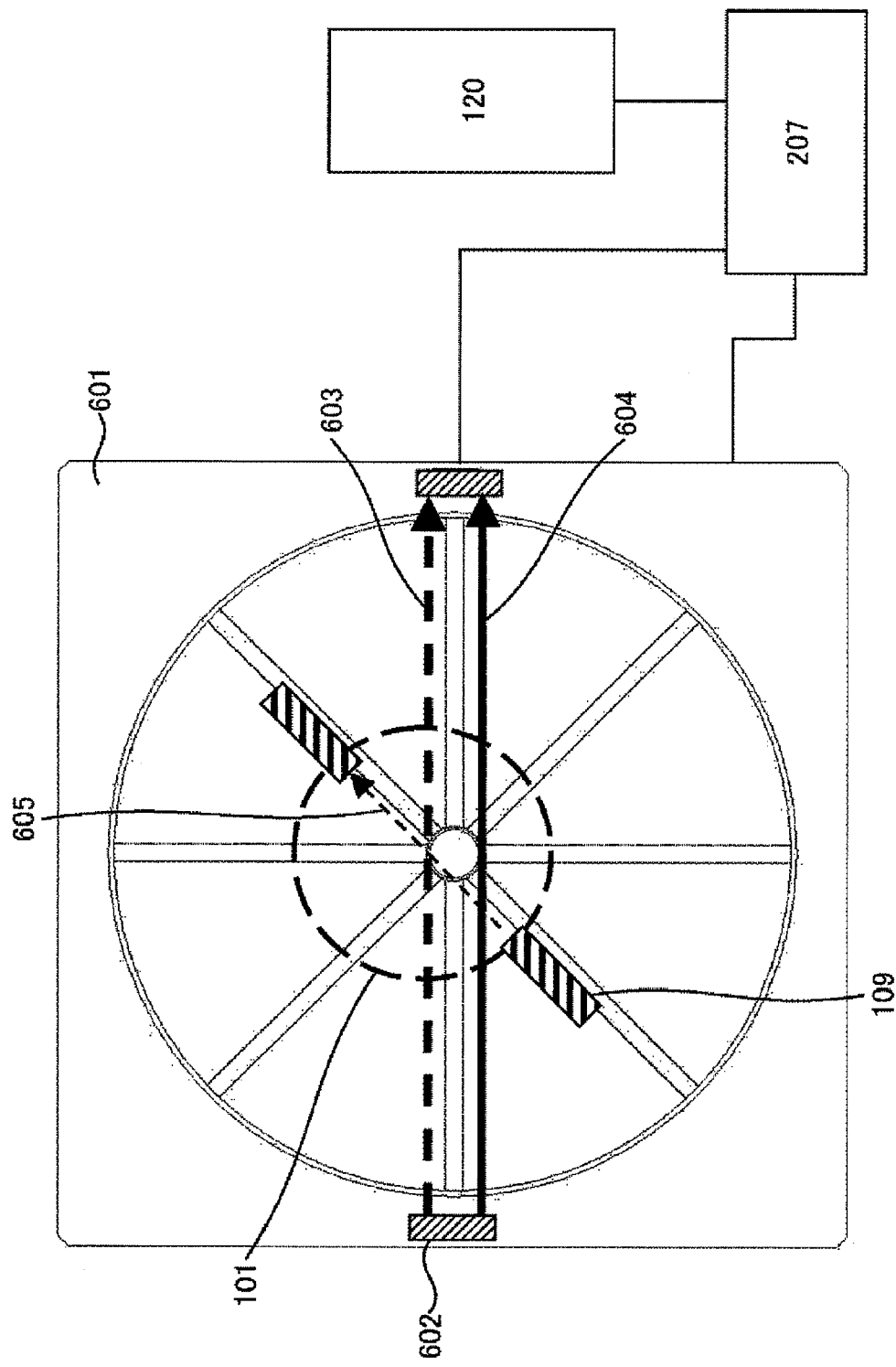
FIG. 6 is a top view of the specimen holding portion in the charged particle beam device of Embodiment 2.

FIG. 6 illustrates a top view of the wafer holding mechanism 601 in superposition with the arrangement of the charged particle column 101. The wafer holding mechanism 601 and the displacement sensor 602 are connected to the temperature regulation mechanism control unit 207 via a signal transmission path, and the temperature regulation mechanism control unit 207 is further connected to the position control unit 120. The primary electron beam reaches around the center of the charged particle column 101 shown by a broken line. When the laser irradiated from the displacement sensor 602 passes through the center of the charged particle column 101, the radiation of the laser is temporarily turned off as shown by a broken line 603. As the mechanism to turn off the laser, the excitation current of laser may be shut off; however, since it may take some time until the laser oscillation is stabilized, shut-down means for physically shutting down the optical path of laser such as a mechanical shutter etc. may be provided. It is noted that in the above described configuration, there will inevitably be a region where the temperature control by diameter measurement of the wafer is not applied; however, by configuring that two beams of laser are irradiated from the displacement sensor, it is possible to measure the diameter of the wafer with one laser while the other is being turned off. FIG. 6 shows a situation in which the laser 603 having an optical path passing through the vicinity of the landing point of electron beam is tuned off, and the laser 604 having another optical path is continuously irradiated.

Furthermore, in the charged particle beam inspection and measurement apparatus for performing wafer processing, it is necessary to take into consideration the disposition of the displacement sensor on the wafer holding mechanism. The charged particle beam inspection and measurement apparatus compatible with wafers is equipped with a height detection sensor 109 as shown in FIG. 1, which is typically based on an optical scheme. Therefore, it is necessary that a pair of the displacement sensors 602 are disposed on the wafer holding mechanism such that the optical path formed between them will not interfere with the optical path formed between the light source of the height detection sensor and its detector. FIG. 6 shows a situation in which the optical path 603 or 604 formed between the pair of displacement sensors is disposed so as not to coincide with the optical path 609 formed between the light source of the height detection sensor and its detector. If the optical path 603 or 604 coincides with the optical path 109 of the height detection sensor, it will become unable to obtain correct height measurement values, and therefore the focusing of the primary electron beam will be hindered.

As so far described, in the present embodiment, the diameter of the wafer 111, that is the expansion/contraction amount of the wafer 111 is measured as needed by the displacement sensor 602, and from the measurement result, the temperature regulation mechanism control unit 207 controls the preset temperature of the temperature regulation mechanism 202. The configuration of the present embodiment enables to prevent the expansion/contraction of the wafer 111 and avoid the position deviation of the observing object.

The present embodiment has an advantage in that the temperature of the wafer can be controlled by directly measuring the expansion/contraction of the wafer 111 which is the primary problem. For example, in Embodiment 1, even if the temperature regulation of the wafer 111 is perfectly performed according to the detection result of the temperature sensor, there is possibility that the wafer does not expand or contract completely thereby resulting in a position deviation. In contrast to that, in the present embodiment, since the expansion/contraction of the wafer 111 is directly measured, it becomes possible to detect not only the expansion/contraction due to temperature, but also faulty holding, position deviations and the like of the wafer 111 due to defects of the static adsorption plate and the like, at the same time.

It is noted that although in the present embodiment, the number of the displacement sensors 602 is assumed to be two as long as the expansion/contraction amount of the wafer 111 can be observed, the number of the displacement sensor is not limited to two, and also any observable measure other than the diameter may be monitored.

Embodiment 3

Although, in Embodiments 1 and 2, the configuration of the charged particle beam device including physical means for measuring an observation indication of the wafer which is necessary for controlling the temperature regulation means has been described, a configuration example of a wafer defect reviewing apparatus which acquires the above described observation indication through image processing will be described in the present embodiment. While, as in Embodiments 1 and 2, description will be made by taking a scanning electron microscope as an example of the charged particle beam device, since the general configuration of the device is similar to that of FIG. 1, description thereof will be omitted.

The wafer defect reviewing apparatus is a charged particle beam device which picks up an image of a defect candidate position by using coordinate information of the defect candidate position detected in the external appearance inspection of the wafer, and performs the processing such as classifying detected defects and detecting critical defects by using the obtained image. First, as in Embodiments 1 and 2, the wafer 111 is transported from a wafer transport apparatus (not shown) to be carried into the load lock chamber 115, which thereafter is evacuated. After completion of evacuation, the wafer 111 is transported onto the wafer holding mechanism 112. Thereafter, the specimen stage 125 moves the measuring target position of the wafer 111 to the irradiation position of the charged particle beam 103 with the position control unit 120. Thereafter, by going through the above described procedure, an image of the observing object is picked up. The picked up image is taken into the image control unit 122, and a defect position coordinate in the image is detected through image processing to calculate the difference between the defect coordinate which is theoretically supposed to be at the center, and an actual center position coordinate. Further, the expansion/contraction amount of the wafer 111 is calculated from the calculated deviation amount of coordinate and the position of the observed defect. According to the determined expansion/contraction amount, the temperature regulation mechanism control unit 207 calculates a temperature rise of the wafer 111 from the accumulated measurement results, and determines a preset temperature of the temperature regulation mechanism 202 to control the temperature of the wafer 111.

Figure 7:
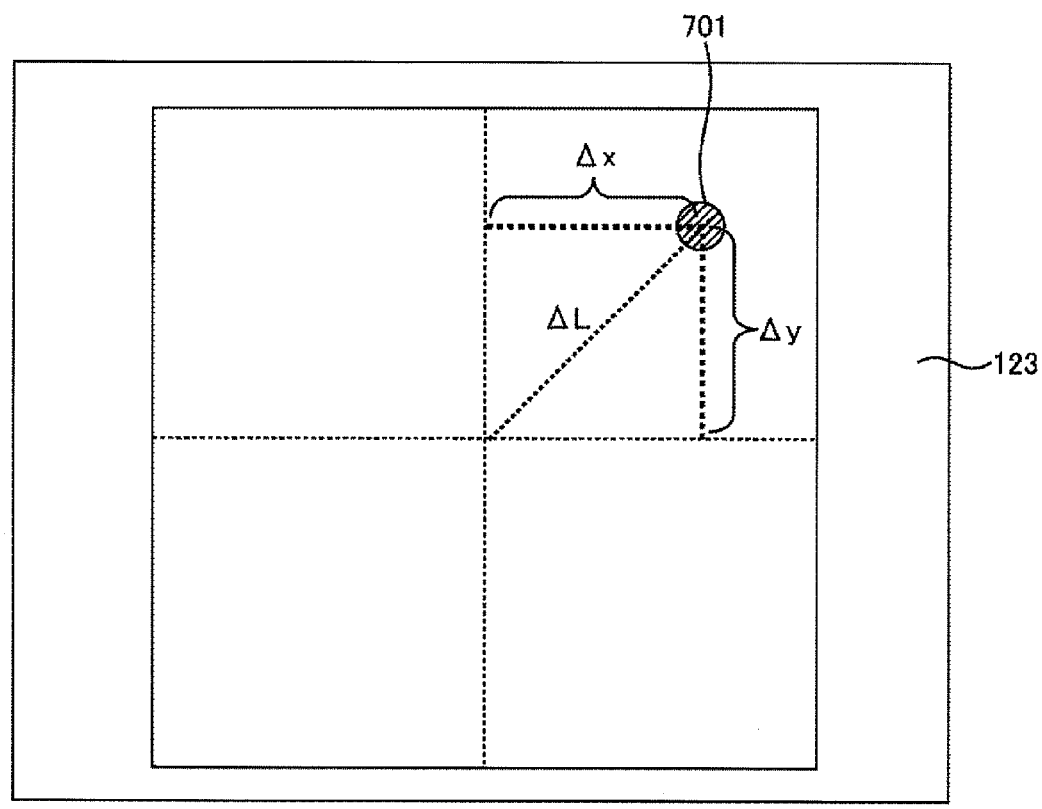
FIG. 7 is a schematic diagram to show the calculation of defect position deviation amount of Embodiment 3.

FIG. 7 shows an example of acquired images. For example, when the coordinates of a defect 701, which is theoretically supposed to be at the center of the screen, are (X, Y) based on the alignment immediately after the loading of the wafer 111, if the position deviation amounts, which are calculated by acquiring image at the image control unit, are Δx and Δy, the expansion/contraction amount and the temperature change of the wafer 111 are determined as shown below.

[Formula 2]

$$\Delta T = \frac{\sqrt{\Delta X^2 + \Delta Y^2}}{\alpha \times \sqrt{X^2 + Y^2}}$$ (Formula 2)

Where, reference symbols denote that ΔT: wafer temperature rise, ΔX: X direction position deviation amount, ΔY: Y direction position deviation amount, α: wafer (Si) linear expansion coefficient, X: ideal defect X coordinate, and Y: ideal defect Y coordinate.

For example, if it is supposed that the ideal defect coordinates are (100, 100) [mm], the deviation amounts of the defect 701 determined from actual image are ΔX=0.001 [mm] and ΔY=0.0001 [mm], substituting these into Equation 1 will result in

[Formula 3]

$$\Delta T = \frac{\sqrt{0.0001^2 + 0.001^2}}{0.0000026 \times \sqrt{100^2 + 100^2}} = 0.38$$ (Formula 3)

which means that temperature has risen by about 0.38° C. Based on this, a preset temperature of the temperature regulation mechanism 202 is determined. Here, although the relationship between the measurement result of position deviation amount from the center and the expansion/contraction amount of the wafer 111 is determined by assuming that the wafer 111 extracts/contracts radially from the center, a relationship which is determined experimentally in advance may be used. Moreover, the calculation of the expansion/contraction amount of the wafer 111 from the position deviation of defect is performed taking into consideration disturbances of magnetic field, and disturbance changes of the charged particle beam 103 due to charged condition of the wafer 111 etc. As described in Embodiment 1, as the result of the specimen stage 125 repeatedly being moved, the temperature of each portion rises to cause the wafer 111 to expand, and thus a position deviation to take place.

In contrast to that, in the present embodiment, since the expansion/contraction amount of the wafer 111 is calculated from the acquired image at the image control unit 122, and from the measurement result, the temperature regulation mechanism control unit 207 controls the preset temperature of the temperature regulation mechanism 202, it becomes possible to prevent the expansion/contraction of the wafer 111, and avoid the position deviation of observing object step-by-step.

In contrast to Embodiments 1 and 2, since the present embodiment does not need physical means for measuring an observation indication of the wafer, which is needed for controlling the temperature regulation means, it offers significant advantages in every aspect of cost such as purchasing, manufacturing, assembling, adjustment and the like.

However, in the present embodiment, since it is necessary to accumulate defect deviation amounts for several points, images in which deviation remains unremoved will be picked up for several points from when deviation is first introduced until when calculation result is reflected. To cope with that, it is configured to be able to select to observe the defect point used for deviation calculation for the second time after finishing defect observation for all the specified points in the wafer 111 surface.

Embodiment 4

In Embodiment 3, since the defect 701 is used as the reference position coordinate for calculating deviation amount, it is necessary that the coordinate information of the defect 701 is known in advance. In the present embodiment, a configuration example in which coordinate information of a specific point on the wafer, for example, a point to be used for alignment is used as reference position coordinate for calculating deviation amount will be described. The general configuration of the equipment is substantially similar to that of FIG. 1.

Figure 8:
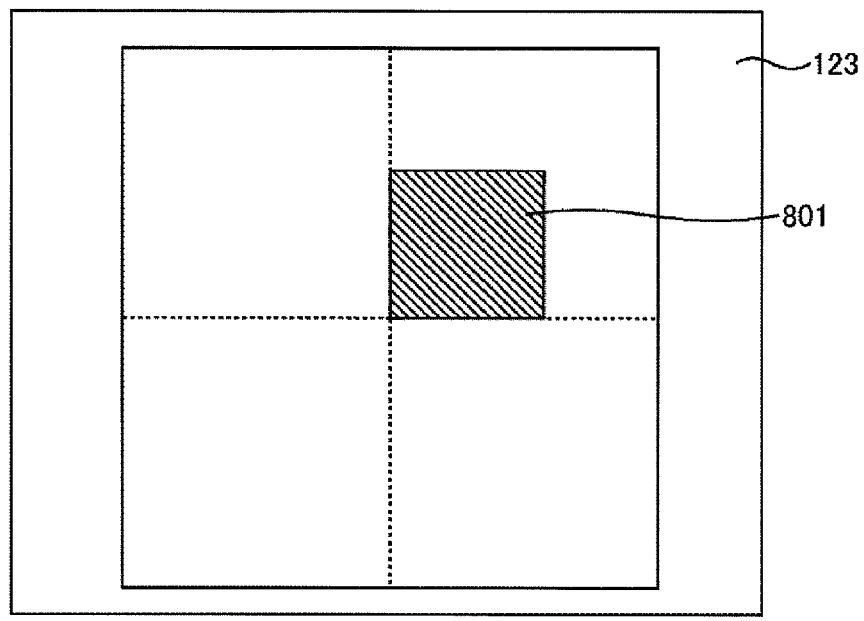
FIG. 8 is a detailed diagram relating to a specific point display at normal time of Embodiment 4.
Figure 9:
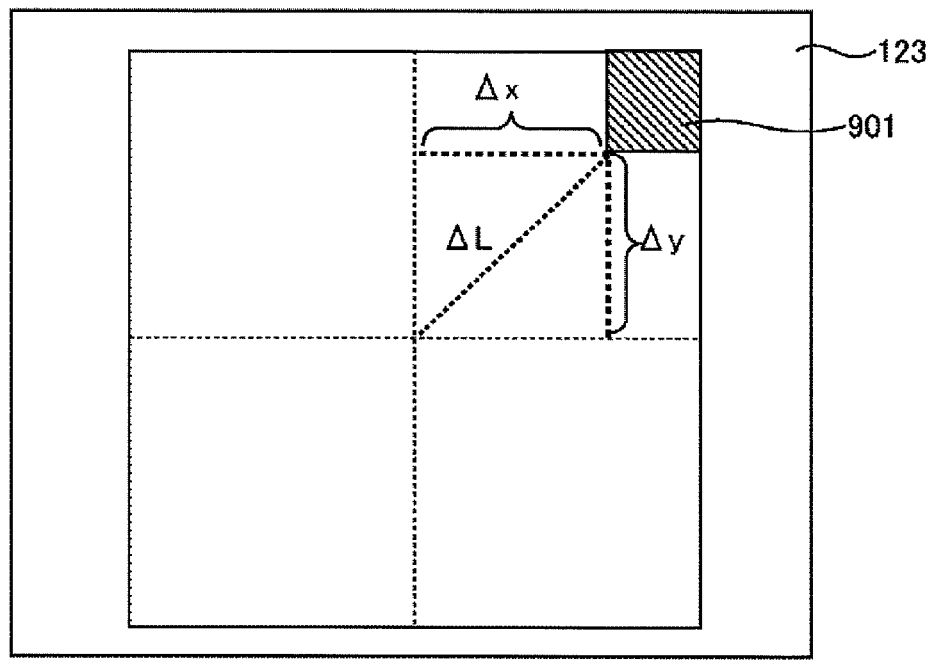
FIG. 9 is a detailed diagram relating to the calculation of specific point position deviation amount of Embodiment 4.

FIGS. 8 and 9 shows an example of the image acquired by a charged particle beam device of the present embodiment. When alignment is performed on a patterned wafer, typically, a point included in the region which includes a characteristic pattern of a wafer 111 of interest as the alignment pattern is preset as a reference point. When moved to alignment point, if the wafer 111 has not been expanded, the registered reference point is displayed at the center of the screen as shown in FIG. 8. On the other hand, when a position deviation has occurred due to thermal expansion of the wafer 111, a position deviation occurs as shown in FIG. 9 so that only a part of the preset region including the alignment pattern is displayed in the field of view. By taking in the deviation amount of this reference point (that is, the difference between the coordinate of the reference point registered in the device, and the coordinate of reference point which is calculated from actually measured image) and the coordinates of the alignment position into the image control unit 122, and substituting them into the equation shown in Embodiment 3, it is possible to determine the temperature change amount of the wafer 111. It is noted that the coordinate position, the number, the measurement timing and the like of the specific point to be used is configured to be selectable by the setting before processing.

Since the configuration of the present embodiment does not need coordinate information of the defect 701, it can be applied not only to a wafer defect reviewing apparatus but also to external appearance inspection apparatuses.

Moreover, while the defect 701 is used as the reference position coordinate in Embodiment 3, the coordinate information of the defect 701 may include the detection error of the defect inspection apparatus which is in the previous stage of the defect reviewing apparatus, there will be no error caused by detection error in the present embodiment. Further, when implementing a fixed point reviewing function, which is new method of using the reviewing apparatus in recent years, in an apparatus, the configuration of the present embodiment will be applicable. Since the information on defect position will not be utilized in the fixed point reviewing function, it is difficult to realize the fixed point reviewing function by the method of Embodiment 3.

As so far described, while the configuration of the means for acquiring the observation indication of the wafer in a contactless manner has been described by using Embodiments 1 to 4, the configurations of these embodiments need not to be used by themselves and may be used in appropriate combination as needed. This will enable to realize an apparatus that has a temperature regulation performance for restricting the expansion/contraction of the wafer 111 more accurately than each configuration of Embodiments 1 to 4 alone thereby allowing the avoidance of position deviation.

INDUSTRIAL APPLICABILITY

The present invention is applicable to charged particle beam devices such as electron microscopes, ion beam processing/observation apparatuses, and the like, and the method for regulating the temperature of a specimen to be observed by a charged particle beam device.

Reference Signs List

| | |
|---|---|
| 101 | Column |
| 102 | Electron gun |
| 103 | Charged particle beam |
| 104 | Electron lens |
| 105, 106 | Deflection coil |
| 107 | Deflection control unit |
| 108 | Object lens |
| 109 | Height detection sensor |
| 110 | Detector |
| 111 | Wafer |
| 112, 601 | Wafer holding mechanism |
| 113 | Interferometer |
| 114 | Specimen chamber |
| 115 | Load lock chamber |
| 116 | Vacuum side gate valve |
| 117 | Vacuum transport robot |
| 118 | Atmospheric side gate valve |
| 119 | Column control unit |
| 120 | Position control unit |
| 121 | Stage control unit |

-continued

Reference Signs List

| | |
|---|---|
| 122 | Image control unit |
| 123 | Monitor |
| 124 | Bar mirror |
| 125 | Specimen stage |
| 202 | Temperature regulation mechanism |
| 203 | Temperature measurement sensor |
| 204 | Electrostatic adsorption plate |
| 207 | Temperature regulation mechanism control unit |
| 208 | Pusher pin |
| 209 | Electrostatic adsorption plate power supply unit |
| 501, 602 | Displacement sensor |
| 603, 604 | Laser beam path of displacement sensor |
| 605 | Optical path of detection sensor |
| 701 | Defect |
| 801, 901 | Alignment region |

The invention claimed is:

1. A charged particle beam device, comprising:
   a specimen holding unit for holding a semiconductor wafer;
   a specimen stage for moving the specimen holding unit;
   a charged beam column having a function to scan a primary charged particle beam onto a semiconductor wafer placed on the specimen stage and to detect generated secondary charged particles to output secondary charged particle signal; and
   a unit for forming an image of the semiconductor wafer from the secondary charged particle signal,
   wherein the charged particle beam device further comprises:
   a temperature regulation unit for controlling a temperature of the semiconductor wafer, and
   a measurement unit for acquiring, in a contactless manner, an observation indication of the wafer that is necessary for controlling the temperature regulation unit,
   wherein the measurement unit includes an information processing unit for performing predetermined processing on pixel data constituting an image of the wafer,
   wherein a position deviation at a specific reference position on the wafer is calculated from the pixel data by the information processing unit, and
   wherein the temperature regulation unit is controlled by using information of the calculated deviation.

2. The charged particle beam device according to claim 1, wherein
   the measurement unit includes a contactless temperature sensor.

3. The charged particle beam device according to claim 2, wherein
   the specimen holding unit includes an electrostatic chuck including an electrostatic adsorption plate, and
   the temperature sensor includes an infrared sensor which is disposed in a through hole formed in the electrostatic adsorption plate.

4. The charged particle beam device according to claim 1, wherein
   the measurement unit includes a unit for measuring a diameter of the semiconductor wafer.

5. The charged particle beam device according to claim 4, wherein
   the charged particle beam device calculates a variation amount of a diameter of the semiconductor wafer from the measured diameter of the wafer, and controls the temperature regulation unit based on the variation amount.

6. The charged particle beam device according to claim 4, wherein
the unit for measuring the diameter of the wafer includes a pair of optical displacement sensors disposed on the specimen holding unit.

7. The charged particle beam device according to claim 6, further comprising:
an optical height sensor for measuring a height of the wafer, wherein
the pair of optical displacement sensors are disposed in a location where an optical axis of a laser beam that is radiated and detected between the pair of sensors does not overlap an optical axis of a laser beam that is radiated and detected by the optical height sensor on the specimen holding unit.

8. The charged particle beam device according to claim 6, wherein
a laser beam radiated from the optical displacement sensor is turned off in a region on the wafer where an optical axis of the primary charged particle beam crosses an optical path of laser beam irradiated from the optical displacement sensor.

9. The charged particle beam device according to claim 6, wherein
the pair of optical displacement sensors are adapted to radiate and detect two laser beams, and
only one of the two laser beams is turned off in a region where an optical axis of the primary charged particle beam crosses an optical path of a laser beam radiated from the optical displacement sensor.

10. The charged particle beam device according to claim 1, wherein
the reference position is a position of a defect which is present on the wafer, or an alignment position.

11. The charged particle beam device according to claim 1, wherein
the temperature regulation unit includes a Peltier element which is disposed on the specimen holding unit.

12. The charged particle beam device according to claim 11, wherein
the Peltier element is disposed radially from a center of the specimen holding unit to an outer periphery thereof.

* * * * *